United States Patent [19]

Ohshoji et al.

[11] Patent Number: 5,022,382

[45] Date of Patent: Jun. 11, 1991

[54] ENDOSCOPE

[75] Inventors: Hiroshi Ohshoji; Fumio Ohshima; Satoshi Matsuo, all of Tochigi, Japan

[73] Assignee: Kabushiki Kaisha Toshiba, Kawasaki, Japan

[21] Appl. No.: 355,748

[22] Filed: May 23, 1989

[30] Foreign Application Priority Data

May 25, 1988 [JP] Japan .................. 63-127600

[51] Int. Cl.⁵ .................................. A61B 1/00
[52] U.S. Cl. ........................................... 128/4
[58] Field of Search .................... 128/4, 5, 6, 7, 8, 9

[56] References Cited

U.S. PATENT DOCUMENTS

| | | | |
|---|---|---|---|
| 3,674,010 | 7/1972 | Falenks | 128/4 |
| 4,246,650 | 10/1981 | Moritani et al. | 368/69 |
| 4,408,598 | 10/1983 | Ueda | 128/4 |
| 4,503,841 | 1/1985 | Tsukaya et al. | 128/4 |
| 4,509,507 | 8/1985 | Yabe | 128/4 |
| 4,648,386 | 7/1987 | Morritt et al. | 128/4 |
| 4,844,052 | 4/1989 | Iwakoshi et al. | 128/4 |

Primary Examiner—Benjamin Layno
Attorney, Agent, or Firm—Foley & Lardner

[57] ABSTRACT

An endoscope including a scope for observing an object, in which at least one of sucking, gas feeding and liquid feeding operations is conducted at the scope, and a time elapsed after a start of the operation is detected by a time detector, and in which the time detected by the time detector is compared with a predetermined reference value, and then the operation is canceled by a canceling device when the time detected by the detected means is at least equal to the predetermined reference value.

4 Claims, 3 Drawing Sheets

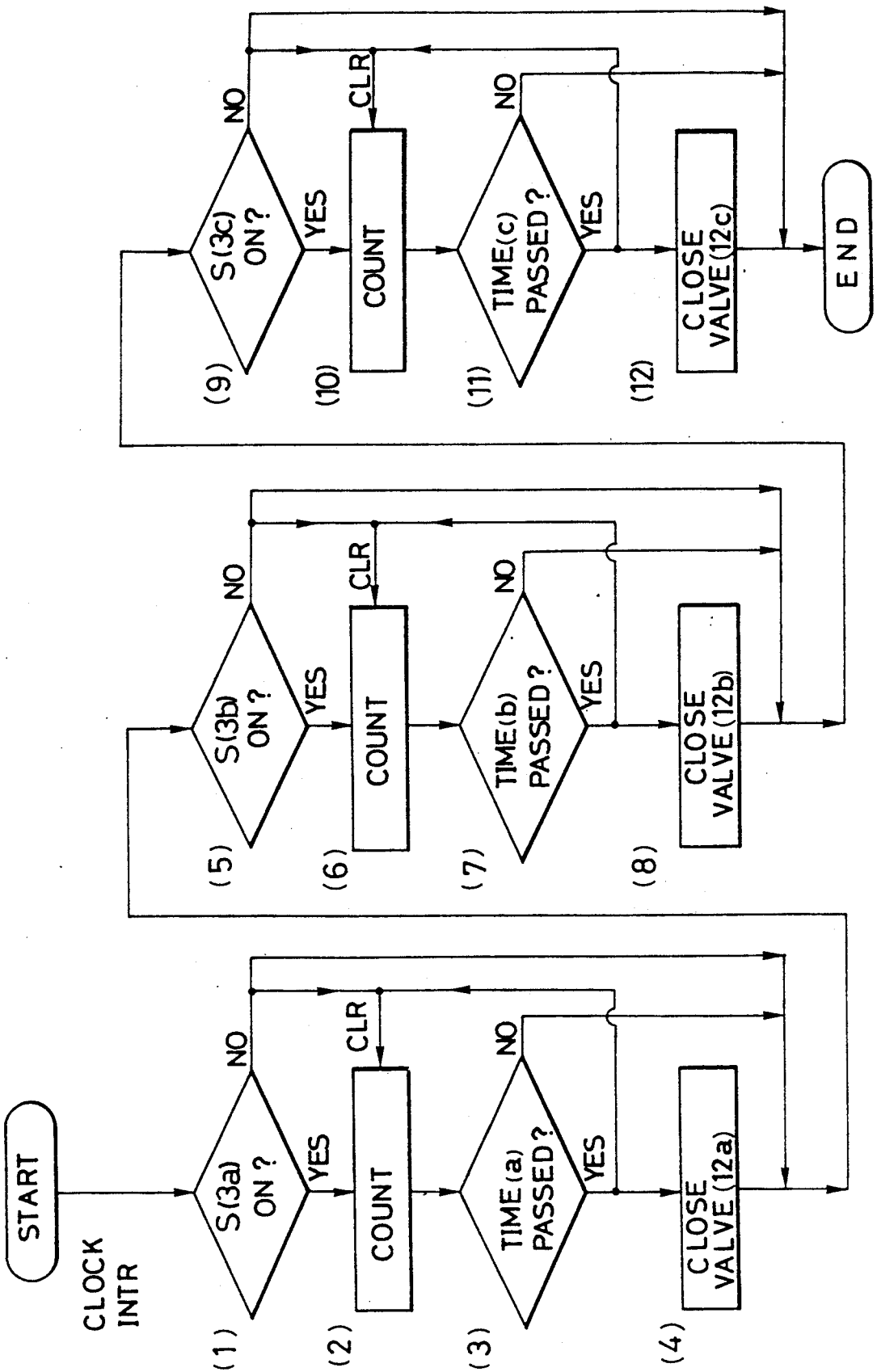

ENDOSCOPE

BACKGROUND OF THE INVENTION

1. Field of the Invention

The present invention relates to an endoscope for use in observing and operating on an internal organ or the like, and more particularly to an endoscope including a device for automatically canceling internal operations such as sucking or the feeding of a gas, a liquid or the like.

2. Description of the Background Art

A conventional endoscope used in observing and operating on internal organ or the like is often provided with devices for carrying out the suction of gas, gastric juice or blood, and feeding a gas, such as the air, or a liquid, such as water, from an end of the scope. For instance, in order to obtain a clear picture image of an object, dirt, such as a gastric juice or blood attached to an end of a scope during a stomach operation is removed by feeding water and thereafter is removed by feeding air to end of scope. Also, a liquid collected in the stomach is discharged by sucking. By feeding air into the stomach, the collapsed stomach is expanded, so as to readily observe its inside.

However, in the conventional endoscope, some problems arise. That is, when the sucking or feeding operation continues for a long time, due to an operation error of an operator or a device, an internal organ of a patient may be damaged or injured to sometimes bring about a serious accident such as a broken organ. For instance, in the feeding operation of a gas such as air, into an internal organ, since the gas can not be visually observed, when, although the feeding operation is stopped by switching off, the operation continues by an error, the gas is increased in the organ to cause a serious accident, such as bursting of the organ. In another case, when the sucking operation is continued for a long time by error, there is a possibility of injury the wall of the organ, such as by puncturing.

SUMMARY OF THE INVENTION

Accordingly, it is an object of the present invention to provide an endoscope, free from the aforementioned defects and disadvantages of the prior art, which includes a device for automatically canceling operations such as sucking or feeding a gas, a liquid within an object to be observed, which is capable of preventing an accident due to an error of an operator and a device for sucking or feeding the gas or liquid.

In accordance with one aspect of the present invention, there is provided an endoscope comprising a, scope for observing an object, means for conducting at least one of sucking, gas feeding and liquid feeding operations at the scope, means for detecting a time elapsed after a start of the operation, means for comparing the time detected by the detecting means with a predetermined reference value, and means for canceling the operation when the time detected by the detected means is at least equal to the predetermined reference value.

BRIEF DESCRIPTION OF THE DRAWINGS

The above and other objects, features and advantaGes of the present invention will more fully appear from the following description of the preferred embodiments with reference to the accompanying drawings, in which:

FIG. 3 is a flow chart for operating the endoscope shown in FIG. 2.

DESCRIPTION OF THE PREFERRED EMBODIMENTS

Figure 1:
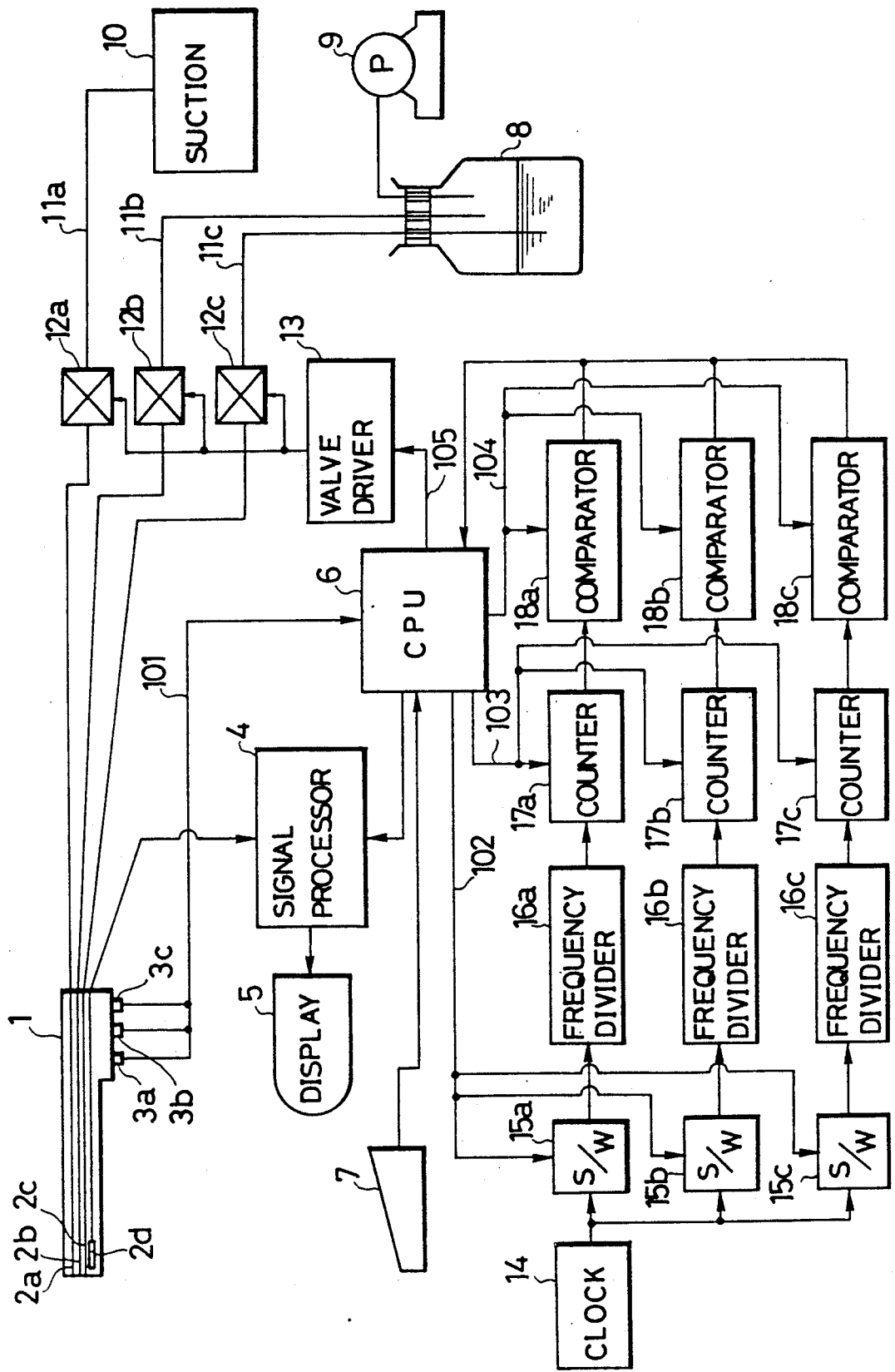
FIG. 1 is a block diagram of a first embodiment of an endoscope according to the present invention.

Referring now to the drawings, there is shown in FIG. 1 the first embodiment of an endoscope according to the present invention, including a device for automatically canceling or stopping operations such as sucking or feeding of a gas, a liquid or the like within an object such as an internal organ of a human body or the like, to be observed by a scope.

In FIG. 1, a scope 1 having three nozzles 2a, 2b and 2c for a sucking, gas feeding and liquid feeding, respectively and a photographing device 2d such as a charge-coupled device (CCD) for picking up picture signals of an object to be observed or operated on, is provided with three switches 3a, 3b and 3c for operating the sucking, gas feeding and liquid feeding functions, respectively, within the object picture picture signals picked up by the photographing device 2d are sent to a signal processor 4 which carries out sampling an analog-digital conversion, writing/reading of the signals in or out of a memory therein. A display 5 for displaying a picture image thereon is connected to the signal processor 4. A central processing unit (CPU) 6 controls the whole system of the endoscope, and the switches 3a, 3b and 3c send ON- or OFF-signals 101 to the CPU 6. A key board 7 for inputting instructions to the CPU 6 is connected thereto.

A liquid container 8 for containing a liquid such as water, for washing the end of the scope, is coupled to a pump 9 for compressing the inside of the container 8 so as to feed a gas, such as air, or water in the container 8 to the nozzle 2b or 2c of the scope 1 through a gas tube 11b or a liquid tube 11c and a magnetic valve 12b or 12c. A suction device 10 such as a vacuum pump is also coupled to the nozzle 2a of the scope 1 through a suction tube 11a and a magnetic valve 12a for sucking the inside of the object. A valve driver 13 is connected between the CPU 6 and magnetic valve 12a, 12b and 12c for controlling their opening and closing in accordance with instructions from CPU 6.

A clock generator 14 outputs a clock signal to three frequency dividers 16a, 16b and 16c through three switch circuits 15a, 15b and 15c which are controlled by a signal 102 fed from the CPU 6 so as to pass or stop the clock signal from the clock generator 14 to the frequency dividers 16a, 16b and 16c when the switches 3a, 3b and 3c are switched on or off, respectively. The frequency dividers 16a, 16b and 16c send a signal to three counters 17a, 17b and 17c, respectively, and the counters count the signals fed from the respective frequency dividers 16a, 16b and 16c. The counters 17a, 17b and 17c output the respective counted numbers to three comparators 18a, 18b and 18c, respectively. In the comparators 18a, 18b and 18c, the counted numbers of the counters 17a, 17b and 17c are compared with reference numbers predetermined, respectively, and the comparison results in the comparators 18a, 18b and 18c are sent to the CPU 6. The CPU 6 discriminates the comparison results of the comparators 18a, 18b and 18c, and controls the valve driver 13 so as to open or close the valves 12a, 12b and 12c when the counted numbers of the counters 17a, 17b and 17c are at least equal to or smaller than the reference numbers predetermined in the comparators 18a, 18b and 18c, respectively.

In this embodiment, the clock generator 14, the switch circuits 15a, 15b and 15c, the frequency dividers 16a, 16b and 16c and the counters 17a, 17b and 17c constitute time detector means, and the comparators 18a, 18b and 18c constitute comparator means. The magnetic valves 12a, 12b and 12c and the valve driver 13 constitute canceling or stopping means.

The control operation of the sucking, gas feeding and liquid feeding of the above described endoscope will now be described.

When at least one of switches 3a, 3b and 3c of the scope 1 is switched on, the switch 3a, 3b or 3c sends signal 101 to the CPU 6, and CPU 6 discriminates ON-OFF states of the switches 3a, 3b and 3c. Then, the CPU 6 sends the signal 105 to the valve driver 13 and controls the valve driver 13 to open the magnetic valve 12a, 12b or 12c corresponding to the switched-on switch 3a, 3b or 3c. At the same time, the CPU 6 sends the signal 102 to the corresponding switch circuit 15a, 15b or 15c to allow the switch circuit 15a, 15b or 15c to pass the clock signal generated by the clock generator 14 to the corresponding frequency divider 16a, 16b or 16c. In this case, the clock generator always outputs the clock signal to the frequency dividers 16a, 16b and 16c through the switch circuits 15a, 15b and 15c at a certain interval as long as the switch circuits 15a, 15b and 15c are opened by the signal 102 sent from the CPU 0.

The frequency divider 16a, 16b or 16c outputs a frequency-divided signal to the counter 17a, 17b or 17c at a certain interval such as 100 ms. and the counter 17a, 17b or 17c counts the number of the signals sent from the frequency divider 16a, 16b or 16c and outputs the counted number to the comparator 18a, 18b or 18c. The comparator 18a, 18b or 18c compares the counted number of the counter 17a, 17b or 17c with the predetermined reference number corresponding to, for instance, 10 seconds, and sends the comparison result to the CPU 6. When the comparison result of the comparator 18a, 18b or 18c indicates that the counted number of the counter 17a, 17b or 17c is smaller than the reference number of the comparator 18a, 18b or 18c, the CPU 6 does not send the signal 105 to the valve driver 13, In turn, when the comparison result of the comparator 18a, 18b or 18c shows that the counted number of the counter 17a, 17b or 17c is equal to or larger than the reference number of the comparator 18a, 18b or 18c, the CPU 6 sends the signal 105 to the valve driver 13 to close the corresponding magnetic valve 12a, 12b or 12c, thereby canceling or stopping sucking, gas feeding or liquid feeding. As a result, when the sucking, gas feeding or liquid feeding operation continues, due to an operation error of an operator or a defective endoscope after the duration predetermined in the comparator 18a, 18b or 18c has passed, such an erroneous operation can be automatically and effectively canceled or stopped, thereby preventing a serious accident to be followed after the erroneous operation.

On the other hand, when the switch 3a, 3b or 3c is switched off before the counted number of the counter 17a, 17b or 17c is smaller than the predetermined reference number in the comparator 18a, 18b or 18c, the. CPU 6 receives the signal 101 from the switch 3a, 3b or 3c, and discriminates the ON-OFF states of the switches 3a, 3b and 3c. Then, the CPU 6 sends the signal 102 to the corresponding switch circuit 15a, 15b or 15c to allow the switch circuit 15a, 15b or 15c to stop the clock pulse from the clock generator 14. Hence, no signal is fed from the frequency divider 16a, 16b or 16c to the counter 17a, 17b or 17c, and the count and comparison are not carried out in the counter 17a, 17b or 17c and the comparator 18a, 18b or 18c. Thus, the CPU 6 does not control the valve driver 13. At the same time, the CPU sends a signal 103 to the counter 17a, 17b or 17c to clear the counted number of the counter 17a, 17b or 17c to reset the initial number thereof.

In this embodiment, the reference numbers predetermined in the comparators can be changed by inputting new reference numbers from the key board 7 to the CPU 6 and then sending a signal 104 from the CPU 6 to the comparators 18a, 18b and 18c. The ON states of the switches 3a, 3b and 3c can be indicated on the display 5, for example by flashing or the like, and the ON-to-OFF change of the switches 3a, 3b and 3c can be also provided to the operator by sounding a buzzer only when the time periods predetermined in the comparators 18a, 18b and 18c have passed. Further, in this embodiment, the automatic canceling of sucking, gas feeding and liquid feeding operations can be done by, for example, feeding an OFF instruction from the key board 7 to the CPU 6 which then sends an always-OFF-signal to the switch circuits 15a, 15b and 15c so as to always allow them to stop the clock signal, by nullifying or ignoring the comparison results of the comparators 18a, 18b and 18c, sent to the CPU 6, or stopping the operations of the counters 17a, 17b and 17c by sending a stop signal from the CPU 6 thereto.

Figure 2:
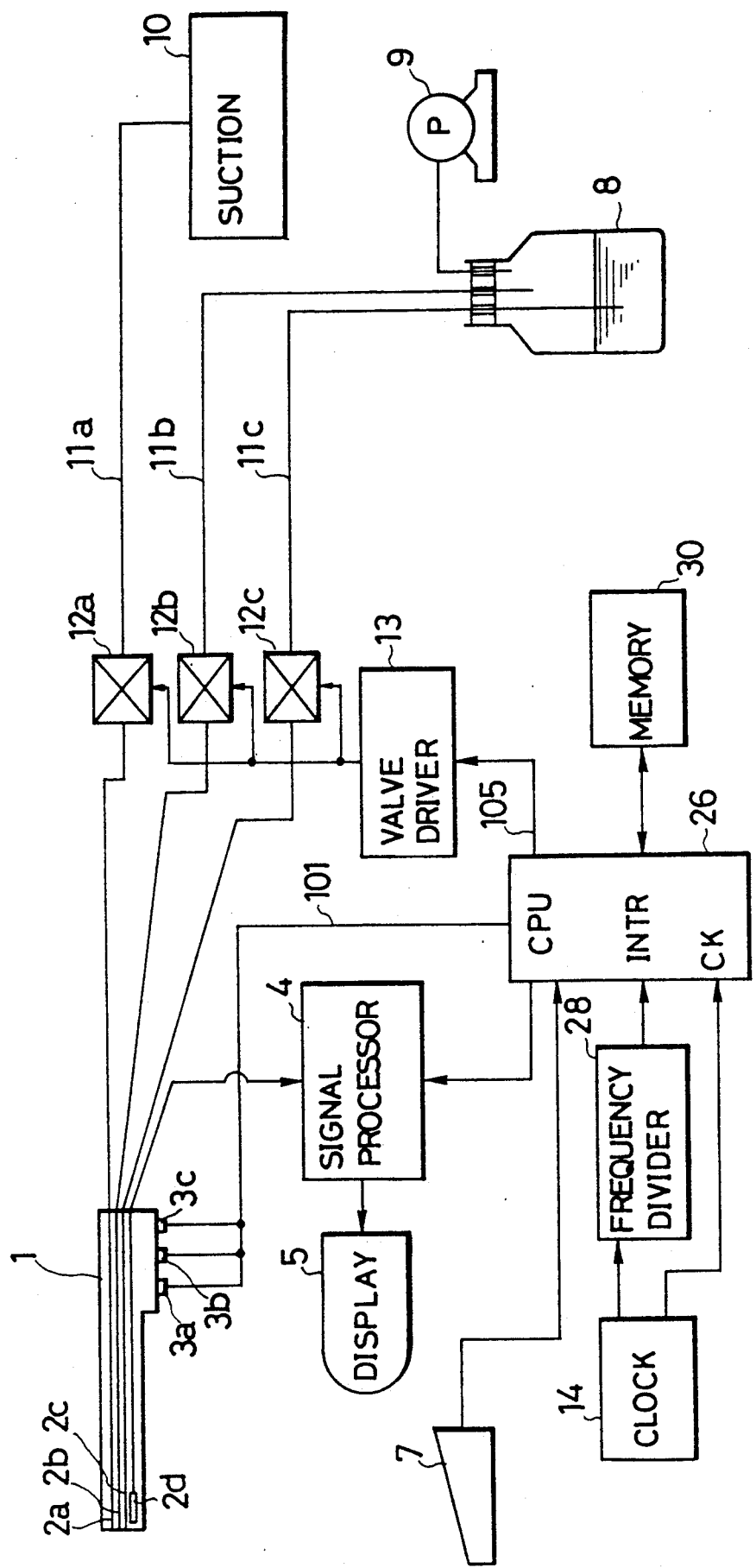
FIG. 2 is a block diagram of a second embodiment of an endoscope according to the present invention.

In FIGS. 2 and 3, there is shown the second embodiment of an endoscope according to the present invention, having the same structure as the first embodiment shown in FIG. 1, except a CPU 26 for controlling the entire system of the endoscope, a frequency divider 28 and a memory 30 for storing a timer count program and a comparison program for comparing between a current count number and a predetermined reference number, instead of the three switch circuits 15a to 15c, the three frequency dividers 16a to 16c, the three counters 17a to 17c and the three comparators 18a to 18c of the first embodiment.

The operation of this embodiment will be described in detail in connection with FIGS. 2 and 3. A clock generator 14 outputs a clock signal as a clock pulse to a CK terminal of the CPU 26 and to the frequency divider 28, and the frequency divider 28 outputs a frequency-divided signal as an interrupting signal to an INTR terminal of the CPU 26 at a certain interval such as 100 ms. When the interrupting signal is fed to the CPU 26, the operation shown in FIG. 3 is started.

That is, when the interrupting signal is fed to the CPU 26, it is discriminated whether the switch 3a is ON in step (1), this is carried out by checking up the signal 101 sent from the switch 3a. When the switch 3a is ON, it follows step (2). When the switch 3a is OFF. the timer count program in step (2) is cleared, and it follows step (5).

In step (2), the CPU 26 reads out the timer count program stored in the memory 30 and carries out this program to increase the count number, and then step (3) is conducted.

In step (3), the CPU 26 reads the comparison program containing the predetermined reference number therein out of the memory 30, and conducts this program. That is, it is discriminated whether the counted number is at least equal to the reference number which is predetermined to a value corresponding to a certain time period such as 10 seconds in the same manner as the first embodiment, i.e., it is discriminated whether the predetermined time period has passed after the switch 3a is switched on. When the counted number is equal to or larger than the reference number, the timer count program in step (2) is cleared and then step (4) is carried out. In turn, when the counted number is smaller than the reference number, it follows step (5).

In step (4), the CPU 26 sends control signal 105 to the valve driver 13, to close the magnetic valve 12a.

Then, steps (5) to (8) are carried out with reference to the switch 3b and the magnetic valve 12b in the same manner as steps (1) to (4) described above, and thereafter steps (9) to (12) are also carried out with reference to the switch 3c and the magnetic valve 12c in the same manner as steps (1) to (4) to finish one set of automatic canceling control of sucking, gas feeding and liquid feeding operations of the endoscope, according to the present invention. It is readily understood that the same effects and advantages as those of the first embodiment can be obtained.

According to the present invention, as described above, when at least one of a sucking, gas feeding and liquid feeding operations of an endoscope to an object is started, time detector means starts, at the same time, to count time elapsed after operation start and sends a counted time to the comparator means, and the comparator means compares the counted time with a predetermined reference value therein. Only when the comparator means discriminates that the counted time is equal to or larger than the reference value, the canceling means stops the sucking, gas feeding or liquid feeding operation, thereby stopping an unexpected operation due to an operation error of an operator or the endoscope. Therefore, such an erroneous operation can be automatically and effectively canceled, to prevent a serious accident to a patient, following the erroneous operation.

Although the present invention has been described in its preferred embodiments with reference to the accompanying drawings, it it readily understood that the present invention is not restricted to the preferred embodiments and that various changes and modifications can be made by those skilled in the art without departing from the spirit and scope of the present invention.

What is claimed is:

1. An endoscope comprising:
a scope for observing an object;
means for simultaneously conducting one or more of sucking, gas feeding and liquid feeding operations through the scope, the conducting means including a suction device connected to the scope via a first line for sucking through the scope, a first valve for carrying out an open-close control of the first line, a container device for containing at least one of a liquid and a gas connected to the scope via a second line, a second valve for carrying out an open-close control of the second line, and a pump device for feeding at least one of a liquid and gas contained in the container device to the scope through the second line and the second valve;
means for detecting the elapsed time after start of each operation, the detecting means including a clock generator for generating a clock signal, a switch circuit switching to pass or stop the clock signal generated by clock generator, a frequency divider for frequency-dividing the clock signals fed from the clock generator, and a counter for counting signals outputted from the frequency divider;
means for comparing the time detected by the detecting means with a predetermined reference value included in the comparing means; and
means for canceling any operation when the time detected by the detecting means is at least equal to the predetermined reference value, the canceling means including a driver device for controlling the open-close control of the first and second valves on the basis of the comparison result of the comparing means.

2. An endoscope comprising:
a scope for observing an object;
means for simultaneously conducting one or more of sucking, gas feeding and liquid feeding operations through the scope, the conducting means including a suction device connected to the scope via a first line for sucking through the scope, a first valve for carrying out an open-close control of the first line, a container device connected to the scope via a second line for containing at least one of a liquid or gas, a second valve for carrying out an open-close control of the second line, and a pump device for feeding at least one of the liquid or gas contained in the container device to the scope through the second line and the second valve;
means for detecting the time elapsed after start of an operation, the detecting means including a clock generator for generating a clock signal, a frequency divider for frequency-dividing the clock signals fed from the clock generator, and a first processor device which counts signals output from the frequency divider using a count program read out of a memory;
means for comparing the time detected by the detecting means with a predetermined reference value, the comparing means including a second processor device which compares the time detected by the detecting means with the predetermined reference value contained in a comparison program read out of the memory; and
means for canceling an ongoing operation when the time detected by the detecting means is at least equal to the predetermined reference value, the canceling means including a driver device for controlling the open-close operation or operations of the first and second valves on the basis of the comparison result of each comparing means.

3. An endoscope comprising:
a scope for internally observing an object or person;
any or all of a sucking apparatus, a liquid supply apparatus and a gas supply apparatus operatively contained within the scope;
a switch means associated with each apparatus to signal its on-off condition;
counter means for measuring and storing the length of time each apparatus has been continuously functioning;
a comparator for comparing each length of time with a predetermined duration of time; and
a switch circuit for terminating the operation of each apparatus which has been functioning continuously for a time equal to or greater than the predetermined duration of time.

4. The endoscope of claim 3, further including means associated with the clock for varying the predetermined time.

* * * * *